United States Patent [19]

Griffin

[11] 4,201,876
[45] May 6, 1980

[54] FLUORINE CONTAINING POLYETHERS

[75] Inventor: Warren R. Griffin, Dayton, Ohio

[73] Assignee: The United States of America as represented by the Secretary of the Air Force, Washington, D.C.

[21] Appl. No.: 748,582

[22] Filed: Dec. 8, 1976

[51] Int. Cl.² ............................................. C07C 43/02
[52] U.S. Cl. ............................... 568/677; 260/544 F; 260/545 R; 260/546; 560/192; 562/596
[58] Field of Search ............ 260/535 H, 484, 615 BF, 260/615 F; 568/677

[56] References Cited

U.S. PATENT DOCUMENTS

| | | | |
|---|---|---|---|
| 3,452,103 | 6/1969 | Trischler | 260/615 BF |
| 3,492,374 | 1/1970 | Le Bleu et al. | 260/615 F |
| 3,699,145 | 10/1972 | Sianesi et al. | 260/535 H |

*Primary Examiner*—Paul J. Killos
*Attorney, Agent, or Firm*—Joseph E. Rusz; Cedric H. Kuhn

[57] ABSTRACT

A fluorinated polyether is synthesized by (1) reacting perfluoroglutryl chloride and 1,5-hexafluoropentane diol to provide a fluorinated polyester and (2) converting ester groups of the polyester to ether groups by $SF_4$ reduction. The product obtained is a thermally stable polyether which is particularly useful in providing an elastomeric material for aircraft fuel tank sealants, tire valves, O-rings, hose, gaskets, and the like.

3 Claims, No Drawings

FLUORINE CONTAINING POLYETHERS

RIGHTS OF THE GOVERNMENT

The invention described herein may be manufactured and used by or for the Government of the United States for all governmental purposes without the payment of any royalty.

FIELD OF THE INVENTION

This invention relates to thermally stable, fluorinated polyethers. In one aspect it relates to a process for preparing the polyethers. In another aspect it relates to thermally and oxidatively stable fluorinated polyether elastomers.

BACKGROUND OF THE INVENTION

A need exists for a material that will meet the requirements for dynamic seal applications, e.g., O-rings, gaskets, diaphragms, and the like, as well as sealant applications, e.g., fuel tank sealants, coatings, and the like, for current and future high performance aircraft. For example, certain advanced aircraft will have hydraulic systems with seals that must withstand temperatures ranging from $-65°$ F. to $400°$ F.

Currently, only a fluorosilicone system is useful in the $-65°$ F. to $400°$ F. range. However, this system is expensive to produce and is only of limited value in seal applications because of its tendency to revert and its poor dynamic performance. This latter deficiency of the system is due to its low tensile strength and low abrasion resistance.

Since the early fluorine work of the 1950's, research has been conducted on fluorocarbon ethers and polymers derived therefrom. Fluorocarbon ether monomers that result in side chains such as perfluoromethylvinyl ether have been incorporated into polymer backbones, but a useful fluorocarbon ether elastomer, such as $+(CF_2)_x-O+_n$, has not been produced. The oligomers that have been prepared indicate a very high cost product.

It is an object of this invention, therefore, to provide novel fluorine-containing polyethers at a substantially lower cost.

Another object of the invention is to provide a process for synthesizing the fluorine-containing polyethers.

A further object of the invention is to provide fluorine-containing polyether elastomers.

Other objects and advantages of the invention will become apparent to those skilled in the art upon consideration of the accompanying disclosure.

SUMMARY OF THE INVENTION

The present invention in one embodiment resides in a fluorine-containing polyether consisting essentially of the following recurring unit:

$$+CF_2(CF_2)_3CF_2OCH_2(CF_2)_3CH_2O+_n \qquad (I)$$

wherein n is an integer representing the number of recurring units. The value of n usually ranges from about 10 to 50 as determined by gel permeation chromotography (GPC).

In another embodiment, the present invention lies in what is essentially a two-step process for preparing the polyether. The steps of the process can be represented by the following equations:

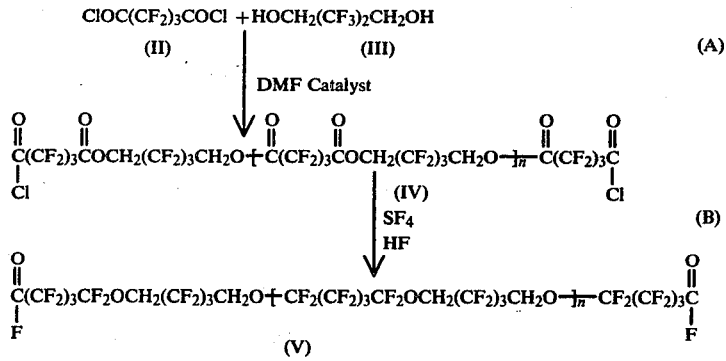

As seen from equation (A), perfluoroglutaryl chloride (II) is initially reacted with 1,5-hexafluoropentane diol (III) in the presence of a catalytic amount of dimethylformamide (DMF). The reaction is carried out under a blanket of an inert gas, such as nitrogen or helium, and it is preferred to react equimolar amounts of compounds (II) and (III). However, it is within the scope of the invention to use a small excess, e.g., 0.1 mole, of one or the other of the reactants. The amount of DMF generally ranges from about 0.5 to 10 milliliters per mole of either of the reactants. The reaction can be conducted over a relatively broad temperature range, e.g., from about room temperature to 200° C., under autogeneous conditions and for a period ranging from about 1 to 24 hours. During the reaction hydrogen chloride is liberated as a gas. At the end of the reaction period when substantially no hydrogen chloride gas is being evolved, there is obtained in high yield a fluorinated polyester as represented by formula (IV) above. During preparation of the polyester and subsequent thereto, care should be exercised to avoid the presence of moisture. If exposed to moisture in the air, it has been found that the polyester degrades. While the polyester is shown by formula (IV) as having acid chloride end groups, at least some of the polyester molecules may have acid end groups because of the presence of moisture in the system.

In the second step of the process, the fluorinated polyester (IV), prepared as described in the preceding paragraph, is reacted with sulfur tetrafluoride using vacuum transfer techniques or in an inert atmosphere and under substantially anhydrous conditions. A molar excess of the sulfur tetrafluoride is utilized, e.g., 1.5 to 5 moles per mole of the polyester. The reaction is preferably carried out in the presence of hydrogen fluoride which functions as a catalyst in the SF$_4$ reduction of the ester groups of the polyester to ether groups. In general, the hydrogen fluoride is used in a catalytic amount which may range from about 0.5 to 2 moles per mole of the polyester. In a preferred procedure, a vacuum is pulled on a closed reaction vessel containing the fluorinated polyester so as to evacuate the air therefrom. The sulfur tetrafluoride and hydrogen fluoride gases are then flowed into the vessel wherein they contact the polyester. The reduction reaction is generally conducted at a temperature in the range of about 50° to 160° C. for a period ranging from about 2 to 24 hours. As a result of the SF$_4$ reduction of the ester groups of the polyester, a fluorinated polyether as represented by formula (V) is obtained as the product of the process.

The fluorinated polyether as depicted by formula (V) above has acid fluoride end groups whereas the polyester intermediate (IV) has acid chloride end groups. The conversion of acid chloride end groups to acid fluoride groups occurs because of the fluorinating effect of sulfur tetrafluoride which is present in the system, and in addition the hydrogen fluoride used as a catalyst. However, it is to be understood that some of the polyether molecules may have acid chloride end groups, i.e., groups derived from the polyester intermediate that are not attacked by the fluorination action. In addition, trace amounts of moisture will convert some of the acid fluoride or acid chloride end groups to acid groups with the liberation of hydrogen fluoride gas or hydrogen chloride gas. Although unnecessary from the standpoint of utility, washing of the fluorinated polyether with water will ensure that its end groups are all acid groups (—COOH).

As mentioned above, the polyester intermediate prepared in the initial step of the present process is unstable in that it degrades when exposed to moisture. However, as a result of the SF$_4$ reduction of ester groups of the polyester to ether groups, a fluorinated polyether is obtained that is thermally and oxidatively stable. The SF$_4$ reduction of ester groups to ether groups so as to provide a stable compound was unexpected since U.S. Pat. No. 2,859,245, which discloses the fluorination of carbonyl groups using sulfur tetrafluoride, teaches that fluorination of ester linkages results in cleavage and additional fluorination.

The fluorinated polyether product of this invention is a liquid polymer which upon curing is converted to an elastomeric material. Prior to curing it is often desirable to subject the polyether to a coupling reaction so as to increase its viscosity. In carrying out the coupling reaction, the polyether product is initially contacted with phosphorus pentachloride (PCl$_5$) at a temperature ranging from about 100° to 150° C. for a period of about 0.5 to 2 hours. The PCl$_5$ reacts with the acid end groups of the polyether, thereby converting them to acid chloride groups. The amount of PCl$_5$ employed is in excess of the amount necessary to obtain the desired conversion, e.g., 2.1 to 3.0 moles per mole of the polyether. Thereafter, the fluorinated polyether with acid chloride end groups is mixed with powdered potassium carbonate (K$_2$CO$_3$). The amount of K$_2$CO$_3$ used is generally less than stoichiometric, ranging from about 1 to 2 moles per moles of the polyether. Upon heating the resulting mixture under a vacuum at a temperature ranging from about 80° to 250° C. for a period of about 4 to 18 hours, a polyether having an increased viscosity is obtained. This increase in viscosity results from polyether molecules being coupled to one another through the reaction of K$_2$CO$_3$ with the acid chloride groups of the molecules. While it is not intended to limit the invention to any particular theory, it is believed that the K$_2$CO$_3$ reacts with the carbonyl groups so that recurring units of the polyether molecules are coupled with one another by —(CF$_2$)$_4$—(CF$_2$)$_4$—groups. In this regard it is noted that infrared analysis of the polyether shows that substantially no carbonyl groups are present.

A more comprehensive understanding of the invention can be obtained by referring to the following illustrative examples which are not intended, however, to be unduly limitative of the invention.

EXAMPLE I

A run was conducted in which a fluorinated polyether of this invention was synthesized. In preparing the polyester intermediate, initially hexafluoropentane-1,5-diol (22.4 g, 0.10 mole) was added to a 50 milliliter, one-necked flask equipped with a magnetic stirring bar and reflux condenser. Dimethylformamide (10 drops) was charged to the flask through the condenser after which perfluoroglutaryl chloride (28.9 g, 0.10 mole) was added in the same manner. The condenser was then topped with a calcium sulfate drying tube. The flask was slowly heated to 190° C., and hydrogen chloride was liberated as the reaction occurred. After the reaction had subsided, heating was terminated and a vacuum was applied until the pressure was reduced to less than 1 mm Hg. When gas evolution had ceased, an infrared spectrum of the viscous, brownish fluid was taken, giving an absorption at 5.6μ assigned to the ester carbonyl. The product (42.9 g, 97.5% yield) slowly solidified on standing.

Analysis—Calc'd for (C$_{10}$H$_9$F$_{12}$O$_4$)$_n$, %: C,28.86; H,0.97. Found, %: C,28.74; H,1.07.

The fluorinated polyester (10.0 g; 0.24 mole), prepared as described in the preceding paragraph, was added to a 100 milliliter stainless steel autoclave. After cooling the vessel and evacuating air therefrom, HF (50 ml, 0.25 mole) and SF$_4$ (39.0 g; 0.36 mole) were added, using vacuum techniques. The autoclave was then heated at 150° to 160° C. for 16 hours. The initial pressure generated was 1200 psig. Excess SF$_4$ and HF were vented at 25° C., and the product was dried at 10$^{-2}$ mm Hg. There remained in the vessel a viscous oil which was transferred therefrom by dissolving with a fluorocarbon solvent (Freon-113). The solution was stored over NaF for 3 hours, filtered and concentrated, yielding 9.8 g (89% yield) of viscous, honey-like clear liquid.

The fluorinated polyether product by infrared analysis showed only a trace of carbonyl absorption. The product had a peak molecular weight of about 4800 as determined by gel permeation chromotography (polystyrene standards). As indicated below, elemental analysis confirmed the structure of the polyether as shown above.

Analysis—Calc'd for (C$_{10}$H$_4$F$_{16}$O$_2$)$_n$,%: C,26.18; H,0.87. Found, %: C,26.02; H,0.85.

EXAMPLE II

A run was conducted for the purpose of increasing by a coupling reaction the viscosity of the fluorinated polyether prepared in Example I. Initially the polyether was treated with an excess of vacuum dried PCl$_5$ in order to convert the polyether's acid end groups to acid chloride groups. The PCl$_5$ was in contact with the polyether for 1 hour at 130° C. A vacuum was then applied. Excess PCl$_5$ sublimed, after gassing of HCl and other by-products had occurred. Vacuum dried, powdered K$_2$CO$_3$ was added to the viscous, acid chloride terminated polyether. The resulting mixture was stirred with a magnetic stirring bar. No outgassing occurred with mild heating (50° C.), but there was an indication of viscosity increase. Heating was terminated and the infrared spectrum of the polyether showed a central large carbonyl. This indicated the structure

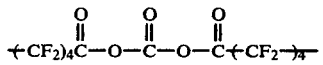

between polyether recurring units. The polyether was thereafter heated to 200° C. under a vacuum. Beginning at 80° C., bubbles of gas began to evolve. When gassing stopped, heating of the polyether was terminated. The polyether product obtained had a higher viscosity than the polyether starting material. The product was dissolved in ether, filtered, and vacuum dried overnight at 100° C. The infrared spectrum of the product showed a very low carbonyl content, indicating a coupling of polyether recurring units with —(CF$_2$)$_4$—(CF$_2$)$_4$ groups.

The polyether, treated as described above, was compounded in accordance with the following recipe:

| Component | Parts by weight |
|---|---|
| Polyether | 100 |
| Silica | 2 |
| Peroxide curing agent[1] | 2 |

[1]α,α'-bis(t-butylperoxy)diisopropylbenzene.

The components of the recipe were mill mixed until a stiff paste with elastomeric properties was obtained. The material was press cured for 1 hour at 340° F. and cooled under pressure, yielding an excellent molding. The molding was post cured overnight at 400° F., providing an elastomer test sheet. Tests indicated that the elastomer had a glass transition temperature (Tg) of −67° C. and a return of rubber properties at −50° C.

Tests were run on samples of the elastomer to determine aging characteristics and physical properties. After being immersed in JP-4 jet fuel for 120 hours at 177° C., a sample showed an eleven percent swell and a shore A hardness of 36. After air aging for 120 hours at 177° C., a sample showed a 1.6 percent weight loss and a shore A hardness of 60. Physical properties of a sample of the elastomer are listed below in the table.

TABLE

| Tensile strength, psi | 176 |
|---|---|
| Elongation, % | 100 |
| Tension set, % | 10 |
| Shore A Hardness | 55 |

As seen from the foregoing, the fluorinated polyethers of this invention are useful in preparing elastomers having good high and low temperature properties as well as good physical properties and resistance to degradation by hydrocarbon fuels. In view of these properties, the fluorocarbon ether elastomers are particularly useful for sealant applications. Utilization of higher molecular weight fluorinated polyethers with selected compounding ingredients provides elastomers of increased tensile strength that have a wide range of uses, such as for O-rings, hose, gaskets, and the like.

As will be evident to those skilled in the art, modifications of the present invention can be made in view of the foregoing disclosure without departing from the spirit and scope of the invention.

I claim:
1. A process for preparing a fluorine-containing polyether which comprises the steps of:
   a. reacting perfluoroglutaryl chloride with 1,5-hexafluoropentane diol in the presence of a catalytic amount of dimethylformamide so as to obtain a fluorinated polyester; and
   b. reacting the fluorinated polyester with sulfur tetrafluoride in the presence of hydrogen fluoride, thereby obtaining a fluorine-containing polyether product.
2. The process according to claim 1 in which substantially equimolar amounts of perfluoroglutaryl chloride and 1,5-hexafluoropentane diol are reacted in the presence of about 0.5 to 10 milliliters of dimethylformamide per mole of either of the aforementioned reactants at a temperature ranging from about room temperature to 200° C. for a period of about 1 to 24 hours.
3. The process according to claim 2 in which the fluorinated polyester is reacted with a molar excess of sulfur tetrafluoride in the presence of 0.5 to 2 moles of hydrogen fluoride per mole of polyester at a temperature in the range of about 50° to 160° C. for a period of about 2 to 24 hours.

* * * * *